United States Patent [19]
Armstrong

[11] Patent Number: 5,350,382
[45] Date of Patent: Sep. 27, 1994

[54] SURGICAL CUTTING GUIDE

[76] Inventor: Jerrold E. A. Armstrong, 1324 Victoria Street, Windsor, Ontario, Canada, N8X 1P1

[21] Appl. No.: 760

[22] Filed: Jan. 5, 1993

[51] Int. Cl.$^5$ ............................................. A61F 5/04
[52] U.S. Cl. ....................................... 606/87; 433/73
[58] Field of Search ................................. 606/79-87, 606/166, 167, 176-179, 96; 30/372, 371; 83/74 S; 433/73

[56] References Cited

U.S. PATENT DOCUMENTS

| | | |
|---|---|---|
| 2,362,741 | 11/1944 | Berke . |
| 3,577,855 | 5/1971 | Baum . |
| 4,211,228 | 7/1980 | Cloutier . |
| 4,335,715 | 6/1982 | Kirkley . |
| 4,342,309 | 8/1982 | Eftekhar ............................ 606/80 |
| 4,515,154 | 5/1985 | Leonard . |
| 4,672,957 | 6/1987 | Hourahane ........................ 606/80 |
| 4,836,779 | 6/1989 | Beu . |
| 5,002,547 | 3/1991 | Poggie et al. . |
| 5,049,149 | 9/1991 | Schmidt . |
| 5,112,334 | 5/1992 | Alchermes et al. . |

*Primary Examiner*—Stephen C. Pellegrino
*Assistant Examiner*—William W. Lewis

[57] ABSTRACT

A cutting guide is provided for use in human maxillofacial surgery. The cutting guide has a bowed body portion adapted to substantially surround the interior surface of the mandible. The body portion has a substantially planar bottom surface to guide a saw blade to cut the mandible in a straight line, one or more elongated pins adapted for insertion into holes created in the mandible to locate the guide in a desired position on the mandible, and a gripper adapted to be gripped by the surgeon to stabilize the guide means while the cut is performed. The body portion is adapted for placement beneath a neurovascular bundle protruding from the surface of the mandible to avoid contact between the saw blade and the neurovascular bundle while the cut is being made. The body portion also includes retracting means to retract the neurovascular bundle to avoid contact with the saw blade.

41 Claims, 4 Drawing Sheets

5,350,382

SURGICAL CUTTING GUIDE

FIELD OF THE INVENTION

This invention relates to cutting guides, and in particular relates to a surgical cutting guide for procedures performed on the human jaw.

BACKGROUND OF THE INVENTION

The bony chin and the associated musculature are recognized as an important source of lower face dysmorphology. Considerable attention in the maxillofacial and plastic surgery literature has been devoted to the diagnosis and treatment of chin deformity. The precision with which antero-posterior deformity and frontal asymmetry can be corrected has resulted in an increase in the demand for achieving technically precise bone cuts. However, the literature is sparse with regard to technical innovation to afford the surgeon a predictable, reproducible and precise chin osteotomy.

Chin recontouring surgery requires the placement of bones into new positions. If a symmetric movement of the chin is to be made in the antero-posterior plane, it is imperative that the osteotomy cuts be straight, of the same length and in the same plane. Otherwise, the movement of the inferior fragment to its new position will result in rotations of the fragment and gaps in the bone-to-bone contact. The result is asymmetry in the position of the chin point and inferior bone healing.

The traditional method of cutting bones in the face has been "freehand" (i.e. without a cutting guide), relying only on the care and technical capability of the surgeon for accuracy. "Freehand" cuts are very difficult to perform and can be rather imprecise, particularly where the cuts are made by two or more surgeons, which is often the case. To facilitate accurate and precise "freehand" surgery, the anterior surface of the mandible is exposed to a greater degree than it ought to be. Although this provides the surgeon with a better view of the entire surgical area to augment the accuracy of bone cutting, it also creates increased access to vital structures, such as the mental nerve or neurovascular bundle, that can be inadvertently damaged during the "freehand" cutting process. The inaccuracies of the "freehand" cutting methods lead to complications such as nerve damage, poor quality bone healing, bone resorption, less than symmetric placement of the chin, instability of the chin, increased operating time and increased blood loss. These significant disadvantages could be reduced or overcome with precise, quick and efficient bone cuts. It is therefore surprising that there has been no known cutting guide developed to perform chin recontouring surgery.

There are numerous prior art devices for precision cutting of bones in the appendicular skeleton, such as cutting guides for the replacement of the hip, knee and the shoulder. These include U.S. Pat. No. 5,049,149 (Schmidt) and U.S. Pat. No. 5,002,547 (Poggie et al.). Without exception, these prior art devices are designed for specific application to the long bones of the appendicular skeleton and are not suitable for cutting the axial skeleton, and in particular the chin, to aid in genioplasty. For example, most prior art guides must be clamped onto the bone being cut or must engage extensive surface areas on the bone for stability. In comparison, the chin is rather small with many vital structures in close proximity, hence it would be very difficult, if not impossible, to securely clamp a guide to the patient's chin or head as taught by the prior art.

What is desired therefore is a surgical cutting guide to be fixed to the anterior surface of the mandible having a guide surface to provide straight and accurate cuts of the mandible. The guide should also be capable of retracting vital elements of the chin to prevent damage thereto. Furthermore, it should reduce inter-operator error where two or more surgeons perform the cutting.

SUMMARY OF THE INVENTION

According to the present invention, there is provided a cutting guide for use in maxillofacial surgery comprising a bowed body portion adapted to substantially surround the anterior sur-face of the mandible, said body portion having:

(i) a means for guiding a saw blade to cut said mandible in a straight line;

(ii) a means to locate the guide in a desired position on said mandible; and (iii) a gripper adapted to be gripped by a user to stabilize said guide means while said cut is performed.

DESCRIPTION OF THE DRAWINGS

A preferred embodiment of the invention will now be described, by way of example only, with reference to the accompanying drawings, wherein.

DESCRIPTION OF PREFERRED EMBODIMENTS

Figure 1:
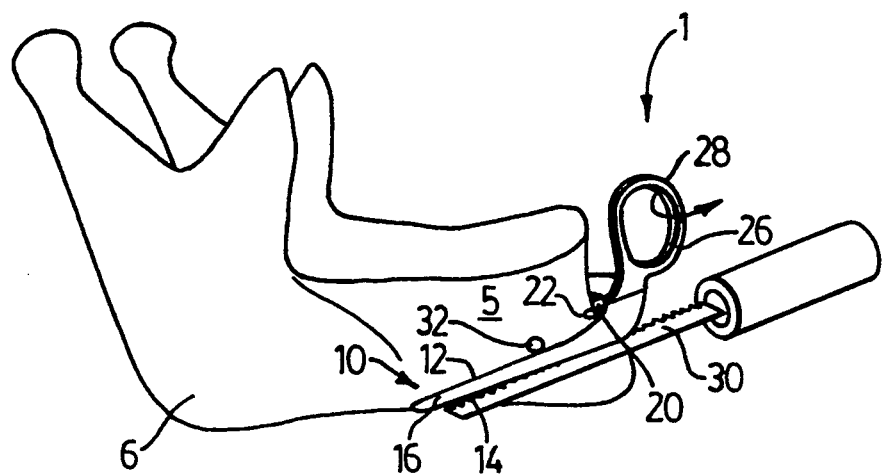
FIG. 1 is a perspective view from the side of a cutting guide according to the present invention placed on an anterior surface of a mandible of a human jaw and a surgeon's saw engaging said guide.
Figure 2:
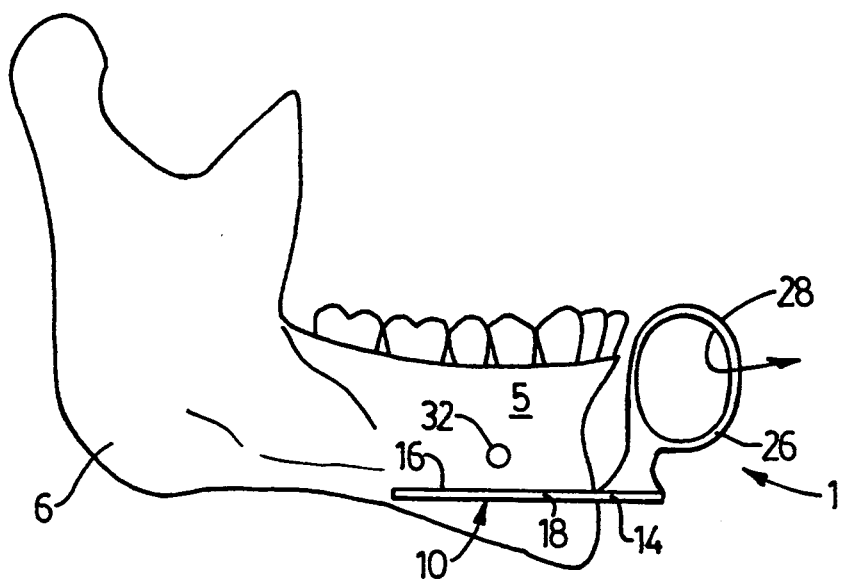
FIGS. 2 and 2a show a side view of the cutting guide of FIG. 1 on the mandible.
Figure 3:
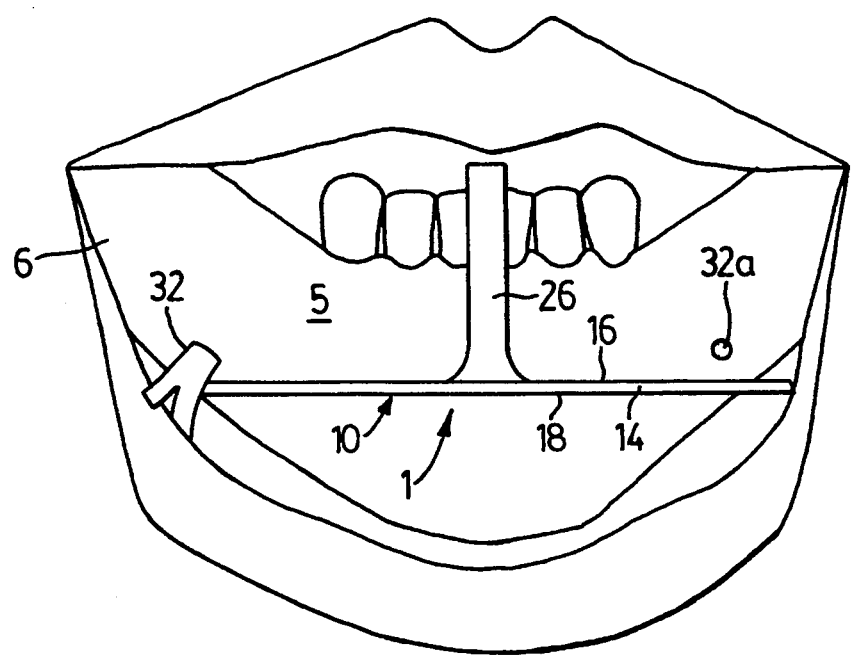
FIG. 3 is an elevational view of the cutting guide of FIG. 1 on the mandible as viewed from the front of the jaw.

Reference is first made to FIGS. 1–3 which show a cutting guide 1 placed on an anterior surface 5 of a human mandible 6. As will be described in greater detail below, the cutting guide 1 is designed for use in maxillofacial surgery to correct chin deformities, also referred to as chin recontouring surgery, genioplasty, functional genioplasty, intraoral genioplasty, anterior mandibular horizontal sliding osteotomy, anterior mandibular osteotomy, mentoplasty, and the like.

Figure 4A:
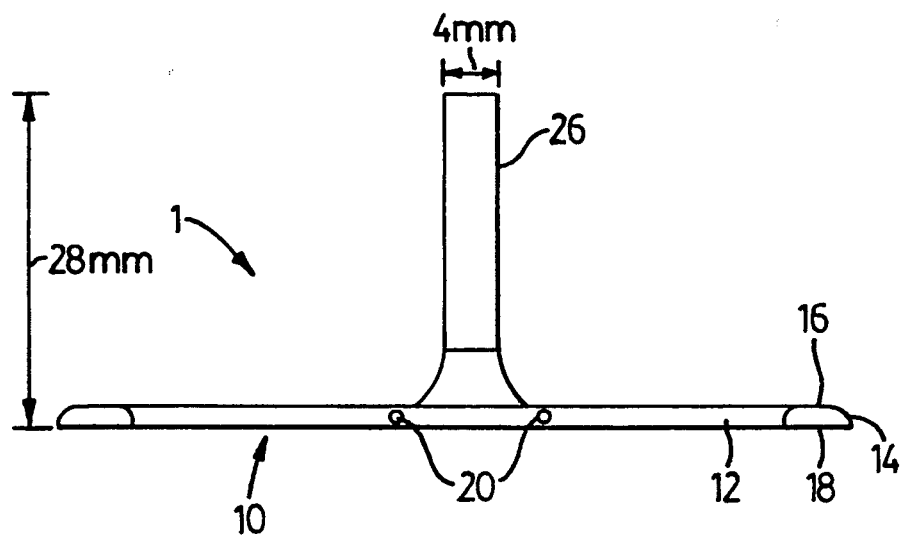
FIGS. 4 and 4a show an elevational view of the cutting guide opposite to that of FIG. 3.
Figure 5A:
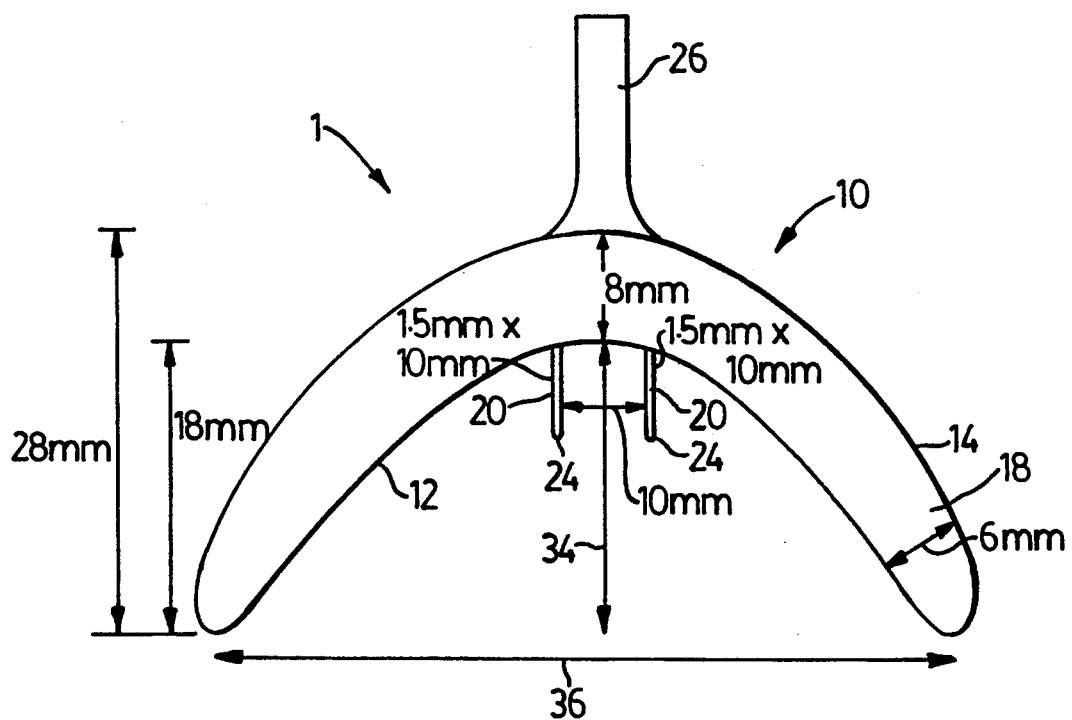
FIGS. 5 and 5a show a view from the bottom of the cutting guide of FIG. 1.
Figure 4:
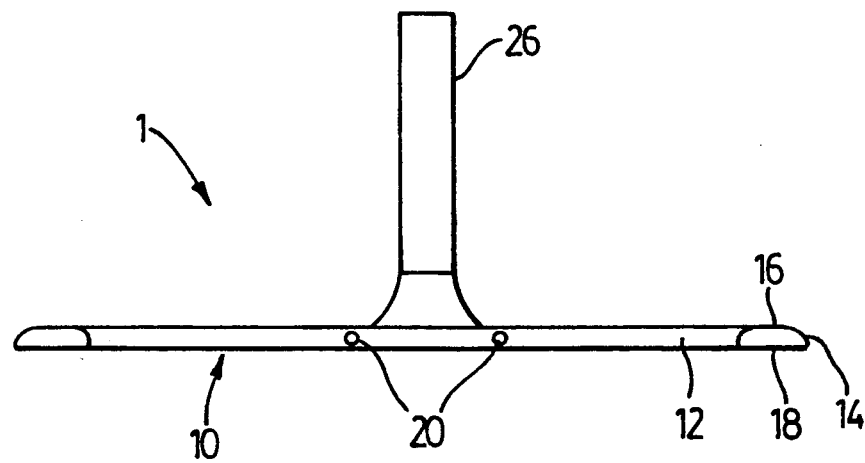
Figure 5:
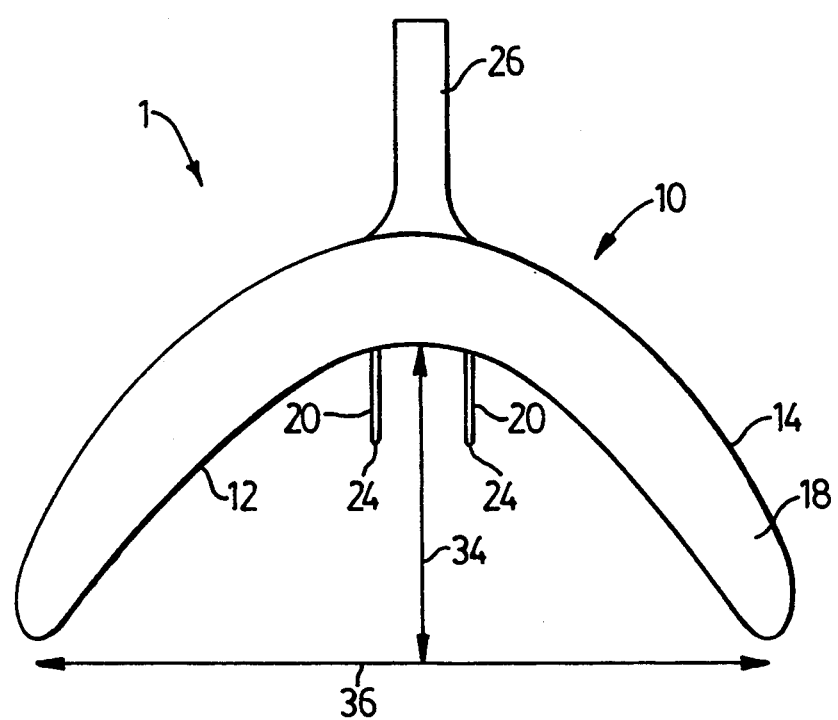

Referring also to FIGS. 4 and 5, the guide 1 has a bowed or generally U-shaped body portion 10 adapted to substantially surround the anterior surface 5. The body portion 10 has a bowed inner periphery or edge 12 adapted for placement adjacent the anterior surface 5, a corresponding bowed outer periphery or edge 14 spaced outwardly from the inner edge 12 and the surface 5, and generally parallel top and bottom surfaces 16, 18 extending between the edges 12, 14. The top surface may also be referred to as the superior or cephalad surface, and the bottom surface may be referred to as the inferior or caudad surface.

The body portion 10 has a means for locating the guide 1 in a desired position on the anterior surface 5 of the mandible 6. In the preferred embodiment, the locating means is in the form of two elongate spaced pins 20 located near the apex or base of the bowed body portion 10. The pins 20 are adapted for insertion into corresponding burr holes 22 created or bored into the mandible 6 by a user, such as a surgeon and resident surgeon, an operating assistant, a medical or dental student, or the like. Each of the pins 20 has a smooth, slender, tubular shape which is tapered at a point 24 furthest from the inside edge 12 to facilitate insertion of the pin 20 into the respective hole 22. The pins 20 are also of an appropriate length, diameter and stiffness to anchor and stabilize the guide in the chin. More than two pins 20 may be provided on the guide 1, although it is desired to minimize the number of holes 22 to be drilled and still maintain three dimensional stability. A single pin 20 may also be used, but is not preferred since the guide's stability may be affected. A purpose of the pins 20 is to reduce or eliminate inter-operator error as discussed below.

The body portion 10 also has a gripper 26 adapted to be gripped by the user to stabilize the guide 1 when in use. The gripper 26 is in the form of a loop connected to the top surface 16 at the apex of the body portion 10 by a short stalk. The gripper 26 is engageable by the user's thumb (as indicated by the arrow 28), normally by the thumb of the user's dominant hand, although either hand may be used. It will be appreciated that the gripper 26 may take various forms and shapes, including that of a tubular handle adapted to be grasped by the user's hand.

It is noted that in the preferred embodiment, the pins 20 are equally spaced on either side of the gripper 26 about 1 cm. apart. It is preferable that the pins 20 be equi-distant or symmetrically located relative to the gripper 26 to avoid rotation of the guide 1 and to reduce bending forces on the pins 20 and the mandible 6 arising during the cutting process due to eccentricities. The pins 20 are located and spaced to also minimize interference with the osteotomy cut or design, and in particular with the creation of a mortise and tenon configuration.

The body portion 10 is further provided with a means for guiding a surgical saw blade 30 to cut the mandible 6. The blade 30 may be that of a reciprocating saw or an oscillating saw, for example. In the preferred embodiment, the guide means comprises a planar bottom surface 18 to enable the user to make a straight and accurate cut in the anterior of the mandible 6. The bottom surface 18 is preferably flat, although it will be appreciated that the bottom surface 18 may have a closely spaced saw-tooth or wavy contour, as long as the crests contracting the saw blade 30 lie along a plane.

Cuts of the mandible to correct chin deformities are made below a mental nerve or neurovascular bundle 32 protruding from the right anterior surface 5 as indicated in FIGS. 1-3. FIG. 3 shows another neurovascular bundle 32a similarly placed (i.e. bi-lateral symmetry) on the left anterior surface, it being understood that any reference to bundle 32 on the right side also applies to bundle 32a. It is desirable to minimize or avoid contact with the bundle 32 (and other vital anatomical parts) during surgery to prevent it from being damaged. Hence, the body portion 10 is adapted to avoid contact between the blade 30 and the bundle 32 by providing a minimum transverse distance or width of the bottom surface 18 (i.e. between the inner and outer edges 12, 14) to avoid rocking of the saw blade 30 while making a cut in the surface 5. To encourage the blade 30 to stay in the plane of the guide surface 18, its minimum width is preferably at least that of the saw blade 30. Although optimally the width of the guide surface 18 should be custom tailored to the particular saw blade used, this is impractical due to the variance in widths of the numerous saw blades used for surgery. Hence, for ease of manufacturing, the guide surface 18 is preferably of one width sufficient to accommodate most blades. It will also be appreciated that the body portion 10 and the guide surface 18 should extend longitudinally from the gripper 26 beyond the bundle 32 toward the back or posterior of the mandible 6 as shown in the drawings.

The body portion 10 is also provided with a means to retract the bundle 32 away from the portion of the mandible 6 being cut to avoid contact with the blade 30. The retraction means may take the form of an obstruction on the body portion 10 between the bundle 32 and guide surface 18. In the preferred embodiment, the obstruction comprises shaping the inner edge 12 of the body portion 10 in the vicinity of the bundle 32 to be closely spaced to the surface 5 of the mandible 6 when the guide 1 is placed thereon. Hence, if the blade 30 is twisted on the guide surface 18 or if it slips off the anterior surface 5 while the cut is being made, the ability of the blade 30 to travel up the mandible 6 toward the bundle 32 is hindered.

For proper retraction to take place, the top surface 16 is used to elevate the bundle 32 out of the surgical field (i.e. the plane of the cut). Although the bundle 32 may hang over the outer edge 14 (as shown in FIG. 3), in another embodiment (not shown) the surface 16 may be made wide enough to avoid any overhang of the bundle 32. Furthermore, the top surface 16 and the inner and outer edges 12, 14, at least in the vicinity of the bundle 32, should be free of sharp protuberances and the like so as to not damage the bundle 32. Hence, the top surface 16 should be smooth and the inner and outer edge 12-14 should be rounded.

Figure 2A:
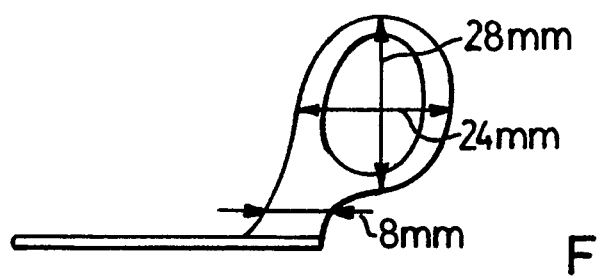

To provide the desired fit of the body portion 10 around the anterior surface 5 of the mandible 6 as described above, the measurements of the inner periphery 12, indicated by the first and second arrows 34 and 36 in FIG. 5, have been determined by studying the Terry Collection of human skulls at the Smithsonian Institute in Washington, D.C., U.S.A.. The first arrow 34 represents the mean distance from the anterior symphysis of the mandible to the mental foramina, and the second arrow 36 represents the transverse dimension of the mandible at the mental foramina. A chin surgeon will preferably have three differently sized guides 1 on hand. One guide 1 will be dimensioned to represent the mean of the population, another guide 1 will be dimensioned two standard deviations more than the mean for larger individuals, and a third guide 1 will be dimensioned two standard deviations less than the mean for smaller individuals. Some sample dimensions of a preferred embodiment are depicted in FIGS. 2a, 4a and 5a.

It will now be appreciated how the preferred embodiment of the cutting guide 1 functions. The surgeon first makes the necessary incisions by standard technique (i.e. transoral incision or other known technique) to expose the anterior surface of the mandible 6. The guide 1 is oriented about the mandible 6 to the desired plane of the cut and the outer cortex of the chin is then penetrated with a drill to create the burr holes 22. The pins 20 are then driven with a mallet through the holes 22 to anchor and stabilize the guide 1 in the chin. Once the vital anatomical parts, such as the neurovascular bundle 32, are retracted on the guide 1 by the user, say the surgeon, the surgeon then further stabilizes the guide 1 by grasping the gripper 26 and begins the required osteotomy cuts. The device's stability therefore reduces or eliminates inter-operator error and increases the accuracy of bilaterally symmetrical bone cuts where two or more users perform different aspects of the cutting and where, in the case of a single user, the user must be reoriented to perform each side of the bone cutting. The resulting increase in surgical efficiency ought to reduce operating time, blood loss, the frequency of postoperative complications and operating costs.

The guide 1 is therefore suitable for resection of symmetric wedges of bone from the paramedian region of the mandible, for use in anterior augmentation, anterosuperior correction, vertical augmentation and reduction in a posterior direction, and the like.

A preferred material for the cutting guide 1 is one which is stiff and can withstand repeated heating and cooling for sterilization and reusability, such as a metal or metal alloy (stainless steel, for example).

Although the present invention has been described with reference to a preferred example thereof, it will be apparent to those skilled in the art that various alterations and modifications may be carried out without departing from the scope of the invention. For instance, replaceable pin-like member could be mounted at spaced intervals along the inner edge 12 which abut the mandible, but do not penetrate the mandible, to further stabilize the guide 1 during use and to further isolate the saw blade 30 from the neurovascular bundle 32. The pin-like members may be further modified to form a continuous replaceable strip mountable on the inner edge 12. It will also be appreciated that the cutting guide 1 may be used for animal/veterinarian purposes.

I claim:

1. A cutting guide for use in human maxillofacial surgery comprising a bowed body portion adapted to substantially surround the anterior surface of the mandible, said body portion having:
   (i) a means for guiding a saw blade to cut said mandible in a straight line comprising a substantially planar bottom surface on said body portion;
   (ii) a means to locate the guide in a desired position on said mandible comprising one or more elongate pins adapted for insertion into holes created in the mandible;
   (iii) a gripper adapted to be gripped by a user to stabilize said guide means while said cut is performed;
   (iv) a bowed inner periphery adapted for placement adjacent the anterior surface of the mandible; and
   (v) a retracting means to retract a neurovascular bundle protruding from the surface of the mandible to avoid contact with said saw while making said cut, said retracting means comprising a part of said inner periphery closely spaced to said mandible and located beneath said bundle while said cut is being made.

2. The cutting guide of claim 1 wherein said body portion is adapted for placement beneath a neurovascular bundle protruding from the surface of the mandible and to avoid contact between said saw blade and said neurovascular bundle while making said cut.

3. The cutting guide of claim 2 wherein a first edge of said bottom surface is defined by said bowed inner periphery and a second edge of said bottom surface is defined by an outer periphery of said body portion spaced from said inner periphery away from said mandible, wherein a minimum distance is provided between said first and second edges to avoid rocking of said saw blade while making said cut.

4. The cutting guide of claim 3 wherein said minimum distance is at least the width of said saw blade.

5. The cutting guide of claim 1 wherein said retracting means includes a portion of a top surface of said body portion.

6. The cutting guide of claim 1 wherein said inner periphery has smooth, rounded edges to avoid cutting the neurovascular bundle.

7. The cutting guide of claim 1 wherein said pins comprise two pins equally spaced on either side of said gripper.

8. The cutting guide of claim 7 wherein said pins are spaced apart about 1 cm.

9. The cutting guide of claim 7 wherein each of said pins forms a smooth, slender, tubular shape which is tapered at its end furthest from said gripper to facilitate insertion of said pin into said hole.

10. The cutting guide of claim 1 wherein said gripper comprises a loop engageable by the user's thumb.

11. The cutting guide of claim 10 wherein said gripper is located at the apex of said bowed body portion on a top surface thereof.

12. The cutting guide of claim 1 wherein said body portion has a substantially planar top surface.

13. The cutting guide of claim 1 wherein said body portion has a bowed inner periphery adapted for placement adjacent the anterior surface of the mandible, said inner periphery having smooth, rounded edges to avoid cutting the neurovascular bundle.

14. A cutting guide for use in human maxillofacial surgery comprising a bowed body portion adapted to substantially surround the anterior surface of the mandible, said body portion having:
   (i) a means for guiding a saw blade to cut said mandible in a straight line comprising a substantially planar bottom surface on said body portion;
   (ii) a means to locate the guide in a desired position on said mandible comprising one or more elongate pins adapted for insertion into holes created in the mandible; and
   (iii) a gripper adapted to be gripped by a user to stabilize said guide means while said cut is performed comprising a loop engageable by the user's thumb.

15. The cutting guide of claim 14 wherein said body portion is adapted for placement beneath a neurovascular bundle protruding from the surface of the mandible and to avoid contact between said saw blade and said neurovascular bundle while making said cut.

16. The cutting guide of claim 15 wherein a first edge of said bottom surface is defined by a bowed inner periphery of said body portion adapted for placement adjacent the anterior surface of the mandible, and a second edge of said bottom surface is defined by an outer periphery of said body portion spaced from said inner periphery away from said mandible, wherein a minimum distance is provided between said first and second edges to avoid rocking of said saw blade while making said cut.

17. The cutting guide of claim 16 wherein said minimum distance is at least the width of said saw blade.

18. The cutting guide of claim 14 wherein said body portion includes retracting means to retract a neurovascular bundle protruding from the surface of the mandible, to avoid contact with said saw while making said cut.

19. The cutting guide of claim 18 wherein said retracting means comprises an obstruction between said neurovascular bundle and said guiding means.

20. The cutting guide of claim 19 wherein said body portion has a bowed inner periphery adapted for placement adjacent the anterior surface of the mandible, and said obstruction comprises a part of said inner periphery adapted to be closely spaced to said mandible and to be located beneath said bundle while said cut is being made, and a portion of a top surface of said body portion.

21. The cutting guide of claim 14 wherein said pins comprise two pins equally spaced on either side of said gripper.

22. The cutting guide of claim 21 wherein said pins are spaced apart about 1 cm.

23. The cutting guide of claim 21 wherein each of said pins forms a smooth, slender, tubular shape which is tapered at its end furthest from said gripper to facilitate insertion of said pin into said hole.

24. The cutting guide of claim 14 wherein said gripper is located at the apex of said bowed body portion on a top surface thereof.

25. The cutting guide of claim 14 wherein said body portion has a substantially planar top surface.

26. A cutting guide for use in human maxillofacial surgery comprising a bowed body portion adapted to substantially surround the anterior surface of the mandible, said body portion having:
    (i) a means for guiding a saw blade to cut said mandible in a straight line;
    (ii) a means to locate the guide in a desired position on said mandible; and
    (iii) a gripper adapted to be gripped by a user to stabilize said guide means while said cut is performed comprising a loop engageable by the user's thumb.

27. The cutting guide of claim 26 wherein said locating means includes one or more elongate pins adapted for insertion into holes created in the mandible.

28. The cutting guide of claim 27 wherein said guiding means comprises a substantially planar bottom surface on said body portion.

29. The cutting guide of claim 28 wherein said body portion is adapted for placement beneath a neurovascular bundle protruding from the surface of the mandible and to avoid contact between said saw blade and said neurovascular bundle while making said cut.

30. The cutting guide of claim 29 wherein a first edge of said bottom surface is defined by a bowed inner periphery of said body portion adapted for placement adjacent the anterior surface of the mandible, and a second edge of said bottom surface is defined by an outer periphery of said body portion spaced from said inner periphery away from said mandible, wherein a minimum distance is provided between said first and second edges to avoid rocking of said saw blade while making said cut.

31. The cutting guide of claim 30 wherein said minimum distance is at least the width of said saw blade.

32. The cutting guide of claim 28 wherein said body portion has a substantially planar top surface.

33. The cutting guide of claim 26 wherein said body portion includes retracting means to retract a neurovascular bundle protruding from the surface of the mandible to avoid contact with said saw while making said cut.

34. The cutting guide of claim 33 wherein said retracting means comprises an obstruction between said neurovascular bundle and said guiding means.

35. The cutting guide of claim 34 wherein said body portion has a bowed inner periphery adapted for placement adjacent the anterior surface of the mandible and said obstruction comprises a part of said inner periphery adapted to be closely spaced to said mandible and to be located beneath said bundle while said cut is being made.

36. The cutting guide of claim 35 wherein said obstruction further includes a portion of a top surface of said body portion.

37. The cutting guide of claim 26 wherein said body portion has a bowed inner periphery adapted for placement adjacent the anterior surface of the mandible, said inner periphery having smooth, rounded edges to avoid cutting a neurovascular bundle protruding from the surface of the mandible.

38. The cutting guide of claim 27 wherein said pins comprise two pins equally spaced on either side of said gripper.

39. The cutting guide of claim 38 wherein said pins are spaced apart about 1 cm.

40. The cutting guide of claim 38 wherein each of said pins forms a smooth, slender, tubular shape which is tapered at its end furthest from said gripper to facilitate insertion of said pin into said hole.

41. The cutting guide of claim 26 wherein said gripper is located at the base of said bowed body portion on a top surface thereof.

* * * * *